(12) United States Patent
Dunsirn et al.

(10) Patent No.: US 10,535,423 B2
(45) Date of Patent: Jan. 14, 2020

(54) MODULE AND SYSTEM FOR MEDICAL INFORMATION MANAGEMENT

(71) Applicants: Baxter International Inc., Deerfield, IL (US); Baxter Healthcare SA, Glattpark (Opfikon) (CH)

(72) Inventors: Todd Dunsirn, Shorewood, WI (US); Doug Frede, Mequon, WI (US); Charles Downey, Milwaukee, WI (US); Kristian Lars Larsen, Milwaukee, WI (US); Tony Klotz, Waukesha, WI (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 964 days.

(21) Appl. No.: 14/323,112

(22) Filed: Jul. 3, 2014

(65) Prior Publication Data

US 2014/0316819 A1 Oct. 23, 2014

Related U.S. Application Data

(63) Continuation-in-part of application No. 13/836,767, filed on Mar. 15, 2013, now abandoned.
(Continued)

(51) Int. Cl.
*G16H 10/60* (2018.01)
*A61M 5/142* (2006.01)
(Continued)

(52) U.S. Cl.
CPC ............ *G16H 10/60* (2018.01); *A61M 5/142* (2013.01); *A61M 5/1723* (2013.01);
(Continued)

(58) Field of Classification Search
CPC ...... G06F 19/322; G06Q 50/24; G16H 50/20; G16H 10/60
(Continued)

(56) References Cited

U.S. PATENT DOCUMENTS 8,666,769 B2 3/2014 Butler et al.
2005/0154615 A1* 7/2005 Rotter .................... G06Q 50/24
705/3
(Continued)

FOREIGN PATENT DOCUMENTS

WO WO-2008140554 A2 * 11/2008 ......... G06F 19/3418

OTHER PUBLICATIONS

Panescu, Dorin, "Emerging Technologies: wireless communication systems for implantable medical devices," IEEE Engineering in Medicine and Biology Magazine, Mar./Apr. 2008 (Year: 2008).*

*Primary Examiner* — John P Go
(74) *Attorney, Agent, or Firm* — K&L Gates LLP

(57) ABSTRACT

A computer module for managing medical information is described. Aspects of the invention provide a "binding" or association process for mapping information from a patient, including at the bedside, to medical devices and/or locations containing medical devices. This may advantageously allow combining all patient-bound device data in a single repository and effectively enable viewing of all patient data in one location. Accordingly, numerous discrete device data with respect to a single patient may be captured, including from among differing medical device types, and conveniently stored together as part of an intelligent data warehouse for efficient retrieval, updating, processing, including with respect to data analytics, display and/or other advantageous features. A medical device communication system is also described.

20 Claims, 11 Drawing Sheets

Related U.S. Application Data

(60) Provisional application No. 61/713,216, filed on Oct. 12, 2012.

(51) Int. Cl.
*A61M 5/172* (2006.01)
*A61B 5/00* (2006.01)
*G06F 19/00* (2018.01)

(52) U.S. Cl.
CPC .... *A61B 5/0022* (2013.01); *A61M 2205/3553* (2013.01); *A61M 2205/3561* (2013.01); *A61M 2205/502* (2013.01); *A61M 2205/52* (2013.01); *G06F 19/3468* (2013.01)

(58) Field of Classification Search
USPC .................................. 705/2–3; 600/300–301
See application file for complete search history.

(56) References Cited

U.S. PATENT DOCUMENTS

| | | | |
|---|---|---|---|
| 2006/0161840 A1* | 7/2006 | Cohen | G06F 17/2264 715/234 |
| 2007/0174087 A1* | 7/2007 | Yeh | G06Q 10/00 705/2 |
| 2008/0091466 A1 | 4/2008 | Butler et al. | |
| 2008/0097550 A1* | 4/2008 | Dicks | A61N 1/37282 607/59 |
| 2010/0169120 A1* | 7/2010 | Herbst | G06Q 50/24 705/3 |
| 2011/0022625 A1 | 1/2011 | Butler et al. | |
| 2011/0077958 A1* | 3/2011 | Breitenstein | G06Q 10/10 705/2 |
| 2011/0077965 A1* | 3/2011 | Nolte | G06Q 10/10 705/3 |
| 2011/0093504 A1 | 4/2011 | Butler et al. | |

\* cited by examiner

MODULE AND SYSTEM FOR MEDICAL INFORMATION MANAGEMENT

CROSS REFERENCE TO RELATED APPLICATIONS

This application is a continuation in part of U.S. patent application Ser. No. 13/836,767, filed on Mar. 15, 2013, entitled "Medical Information Management System," which claims priority from U.S. Provisional Application No. 61/713,216, filed Oct. 12, 2012. The entireties of each of the foregoing applications are incorporated herein by reference.

BACKGROUND OF THE INVENTION

The present invention is related to the field of communication (retrieval and sending of data) and storage of medical information commonly received from medical devices in the hospital environment. Conventional technology requires that separate servers and databases be employed for storage of information received from each type of device, or each manufacturer of a device. For example, a heart monitor may be equipped to output the sensed signal which may be sent to a server and stored into a database. A medical drug pump may also be configured to output a signal regarding dosage levels supplied to a patient. Conventional technology does not allow the output from the drug pump and the heart monitor to be commonly stored and commonly readable in the same database. Different manufacturers may program their own devices with proprietary software that requires specialized databases in order for the output to be readable and properly archived in a database. Currently, health care facilities may employ several different proprietary servers and databases for all the various types and brands of machinery commonly used in a hospital environment.

SUMMARY AND OBJECTS OF THE INVENTION

By way of summary, the present invention is directed to the management of medical device and medical related information. An effect of the present invention is to collect information from a multitude of medical devices and sources on a common network and make it available to qualified individuals. A primary object of the invention is to provide an apparatus that may collect, send, archive, and categorize information from any device. An additional object of the invention is to have a single data management system that is capable of receiving information transmitted using a wired or wireless connection (hereinafter referred to as wireless for convenience) from any device used in the medical field and allow qualified users to access that information.

The medical information management system includes a central database programmed to send and receive data to and from a plurality of medical devices. The medical devices may include, but are not limited to, medical diagnostic equipment, medical pumps, medical imaging devices, and any device capable of gathering information from a hospital patient.

The medical devices may be programmed with software allowing them to wirelessly input data to the central database. Configuring the medical devices to communicate wirelessly with the central database allows, for example, ambulances to be equipped with medical diagnostic and treatment devices that communicate with the central database over a wireless network.

The central database may be located anywhere and accessible on a server via the internet. Accordingly, the central database may be implemented within "the cloud," meaning that computing servers and/or data storage capacity is provided on demand using a large number of distributed systems. The cloud allows users to avoid the cost of a huge datacenter while simultaneously allowing for rapid growth if needed. The cloud may be specifically configured by a medical company for use with its product or the cloud may be any generic storage space that is accessible via the internet. Having a cloud contain the central database further facilitates access to the underlying data since it enables remote access with any device equipped with telematic software and hardware. The telematic equipment may be retrofitted of into any existing medical device or may be built into the device during manufacturing.

The term telematics is known to include devices that utilize telecommunication technology, as well as the internet, for the purpose of transmitting and storing information. Telematics may also include allowing wireless, remote control of an object using telecommunication and internet technology. Additionally, telematics may include any technology used to communicate such as satellite or radio communication.

A handshake device programmed in the central server and database translates all received data into a language that is readable and interchangeable by a multitude of devices. One example of such a device may include a nurse's station or electronic health record. The handshake device allows one, common software to be used to track and compartmentalize all received data to the central server. This prevents situations requiring multiple databases and multiple software programs to read, track, and store all the different information received by the nurse's station. The same principle may be applied to the entire hospital's information infrastructure, allowing a seamless integration of all information that is gathered from medical devices. Delivery of the information may be facilitated using a subscription service that allows certain users and systems to subscribe to the information of interest.

A filtering device in communication with the central database may be used as well. The filtering device may include software programmed on the central database, or anywhere else, and programmed to filter the data into various groups of distinguished categories. This allows the data to be easily stored and to link related data together. The filtering device prevents a qualified person from having to sift through data to search for a single piece of information. For example, if the amount of morphine administered over the course of a month is desired, the filter device may be used to gather and store all data relating to the quantity of morphine administered based on a common identifier such as the patient name, room or bed id, but is not limited to these types of identifiers. For reasons such as this, the filtering device may be programmed as the administration sees fit, and custom tailored to the specific needs of the organization. It does not matter what device or what manufacturer supplies the information. The handshake device and filtering device may make the data all commonly readable by a single device including a personal computer, a smart phone, and a tablet computer or any other related device.

The server and database may also include data mining applications configured to allow users and/or the server to gather information from other devices associated with a patient that may be related to a particular event, such as the delivery of morphine described above. The data mining applications allow users to easily determine the effect that the morphine delivery had on, for example, heart rate, blood pressure, SPO2, and other vitals.

One example of a medical device that may benefit from this technology includes a medical liquid pump. Medical liquid pumps are commonly used in the medical field to administer liquid medication, nutrition, blood, etc. The pump may be manufactured or retrofitted with telematic software and hardware to allow it to communicate with the central database. A message listener device may be programmed to wirelessly receive messages from any number of medical pumps in operation. These pumps may be inside ambulances, in emergency moms, in patient rooms, or anywhere. A message distribution device may include a message queue to store messages and a message broker to allow the hospital to deliver the messages following receipt and processing by the medical information management system as described in detail below, that are received by the central database to a plurality of locations including an operational database like the hospital's main system database, an analytics database, and an integration engine. The system database may be programmed to extract data from outside sources, transform it to fit operational needs (which can include quality levels), and load it into the end target (database, more specifically, operational data store, data mart or data warehouse). This process is commonly referred to as ETL in the industry. Reports may then be generated following the ETL stage.

The analytics database may compute and display real time analytic information using an analytics engine. An integration engine may be programmed to transmit the messages and receive a plurality of feedback from a central information system through the use of a specific integration partner plug in which allows communication with Cerner, Epic, or other databases. The central information system may include a regional system that is responsible for many health care facilities or any other overseeing entity such as Cerner or Epic. The hospital's main information system database may then be programmed to produce orders for pumps anywhere in the field. An order broker implemented by the medical information management system may then transmit the orders wirelessly to each pump. The orders may include a drug library with a plurality of drugs identified as well as dosage information for a particular patient. A file distribution broker programmed on the central database assigns the proper pump with its specific order. A health care provider may then receive the order wirelessly on the pump as it displays the order with the necessary drug's information.

The pumps may further each include a locator allowing the central database and the hospitals main system database to communicate wirelessly with the pump and determine the geographic location of each one of the medical pumps.

In order to periodically update the pumps in the field, a software uploading device may be programmed to wirelessly transmit software to each one of the medical pumps as well as updated drug libraries with current lists of drug information.

Real time monitoring devices located in each one of the medical pumps may be programmed to receive sensed information from sensors and wirelessly transmit the sensed information to the central database where it may be accessed by the hospital's main system database. The sensed information may include, but is not limited to, blood pressure, pulse, temperature, heart rhythm or any other diagnostic information.

A compliance device in each one of the pumps may be programmed to monitor the pump's operation and verify orders are successfully executed. Reports may then be generated by the compliance device and wirelessly transmitted a message listener on the central server that may also be accessed by the hospital's main system database.

Any information gathered or stored on the central database may be made easily accessible to the hospital's main system database with the handshake and filtering device discussed above. The system not only collects and transmits medical device information but also provides a central management tool for all of an organizations medical devices. This centralization allows management of the population of medical devices and access to both the devices and their information in one location. Additionally, the procedures mentioned above with respect to the medical liquid pumps may be employed on any medical device. The invention allows for the procedure to also be retrofitted on any existing device that is manufactured by any company.

Aspects of the invention provide a "binding" or association process for mapping information from a patient, including at the bedside, to medical devices and/or locations containing medical devices. This may advantageously allow combining all patient-bound device data in a single repository and effectively enable viewing of all patient data in one location. Accordingly, numerous discrete device data with respect to a single patient may be captured, including from among differing medical device types, and conveniently stored together as part of an intelligent data warehouse for efficient retrieval, updating, processing, including with respect to data analytics, display and/or other advantageous features. A medical device communication system is also provided.

Binding may location-based, device-based or mixed. In location-based binding, a device may be associated to a location; when a patient is also bound to the same location, then a binding between the device and patient is created. In device-based binding, binding from a patient goes directly to the device. Mixed-based binding uses both location and device-based binding.

Medical devices may typically be continuously networked for integration with the binder service. Such devices may be connected to a central gateway or have wired/wireless network capabilities. They may also be associated with a patient for an extended period of time, such as patient monitor, infusion pumps, and so forth. Alternatively, medical devices could also be episodic devices that may typically be used for a single set of measurements at a given time and then transferred for use with another patient, such as vitals monitor on roll stand, height/weight scale. Also, medical devices could be continuous stand-alone devices which may be associated with a patient for an extended period during a treatment session, though not connected directly to a gateway or network, such as a ventilator, so long as such devices are adaptable to an interface for communicating information to a network.

Admit Discharge Transfer ("ADT") information, such as an HL7 ADT feed, may be used to provide binding services. This could be used particularly when a device has high acuity and its messaging can provide a location identifier. The ADT feed may provide patient information with current location identifier.

A device may be manually bound, such as by a clinician, via a binder User Interface ("UI"). This method could include use of a barcode scanner, a keypad input, a drop-down UI, such as if a device provides ADT information.

Binding could also be accomplished automatically, such as using a third-party application. To accomplish this, the application may interface through a binder Application Program Interface ("API"). Binding could also be accomplished using a patient's Electronic Medical Record ("EMR").

When a device is able to read and store a patient identifier, binding could be done directly thorough the device. This may be ideal, for example, with episodic devices. This method could include use of a barcode scanner, a keypad input, a dropdown UI, such as if a device provides ADT information.

Unbinding may be performed manually or automatically. For manual unbinding, a device may be manually unbound by a clinician, such as through a device UI, a binder API or a clinician UI to the binder service. For automatic unbinding, unbinding may be triggered by particular information from an ADT feed, such as to discharge or transfer a patient. Unbinding may also occur automatically when a patient is unbound from a device/location elsewhere, or automatically unbound from a device after some period of time following receipt of a message from the device, or unbound after a single or particular set of messages and/or measurements are received and/or charted.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
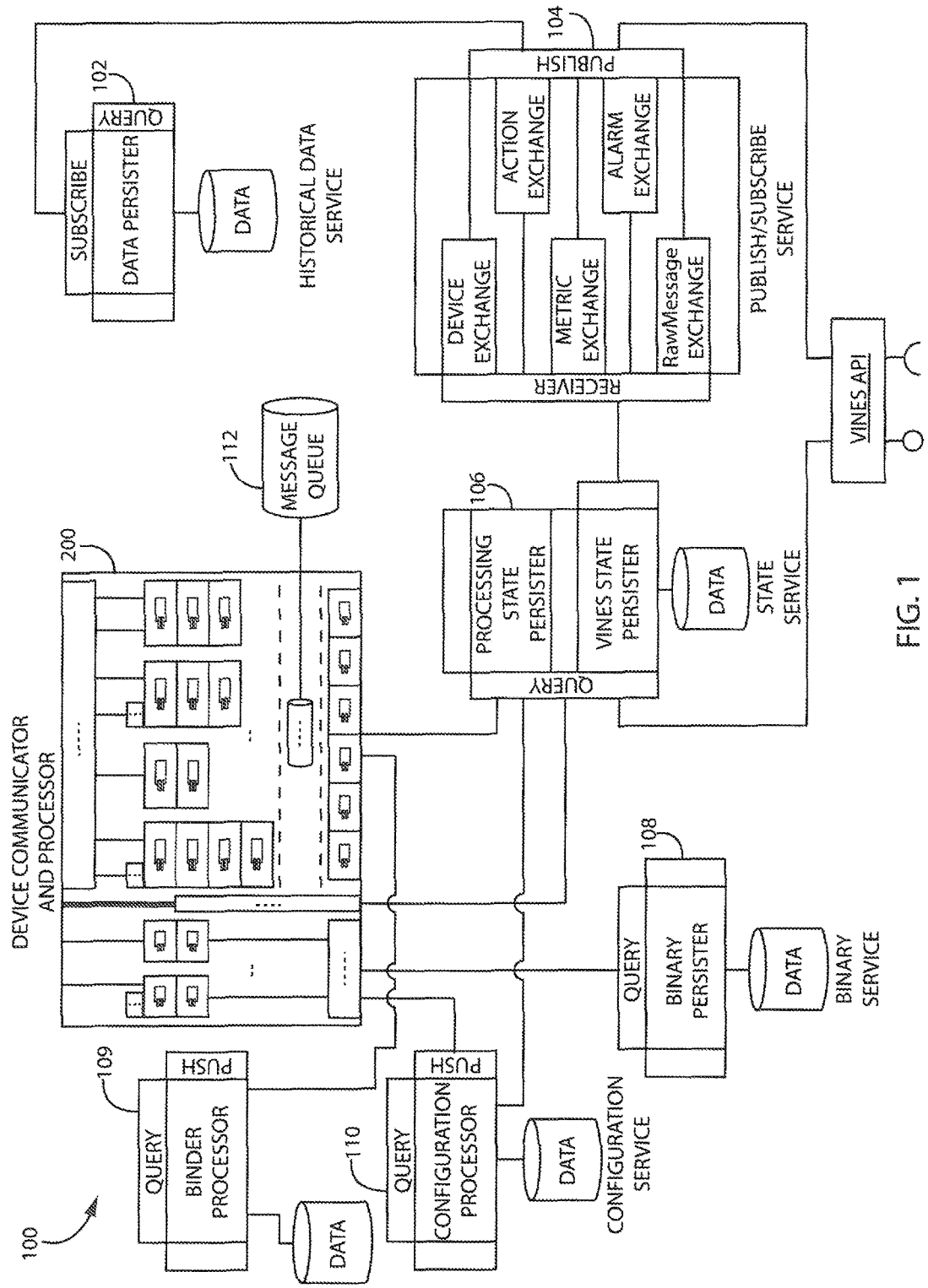
FIG. 1 is a schematic illustration of a device communication application which may be referred to as a vendor neutral enterprise system, or ViNES, according to an exemplary embodiment.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words "connected", "attached", or terms similar thereto are often used. They are not limited to direct connection but include connection through other elements where such connection is recognized as being equivalent by those skilled in the art.

DETAILED DESCRIPTION OF EMBODIMENTS

The present invention and the various features and advantageous details thereof are explained more fully with reference to the non-limiting embodiments described in detail in the following description.

1. System Overview

Referring now to FIG. 1, one example of the invention includes a device communication application 100 which may be referred to as a vendor neutral enterprise system, or ViNES, according to an exemplary embodiment. The core functionality of ViNES will allow deployed medical devices to connect to and communication engine to connect from, a set of installable modules could allow common functions such as: device management, data reporting, integration support, and real-time monitoring. Accordingly, application 100 include a device communicator and processor 200, described in further detail below with reference to FIG. 2, a historical data service 102, a publish and subscribe service 104, a state service 106, a binary service 108, a binder service 109, and a configuration service 110.

Application 100 may be implemented using one or more standard computer systems including a computer processor, memory, and input and output devices. The memory can include both short term random access memory (RAM) and long term storage, such as a disk drive. Input and output device can include keyboards, monitor, data connections such as the Internet, etc.

ViNES application 100 may be designed to accommodate not only medical infusion pumps, but a broad spectrum of medical devices which may include respirators, patient monitors, and more. Additionally, the invention may not be limited to a single device manufacture, but may be employed to a broad range of devices by different manufacturers.

Figure 2:
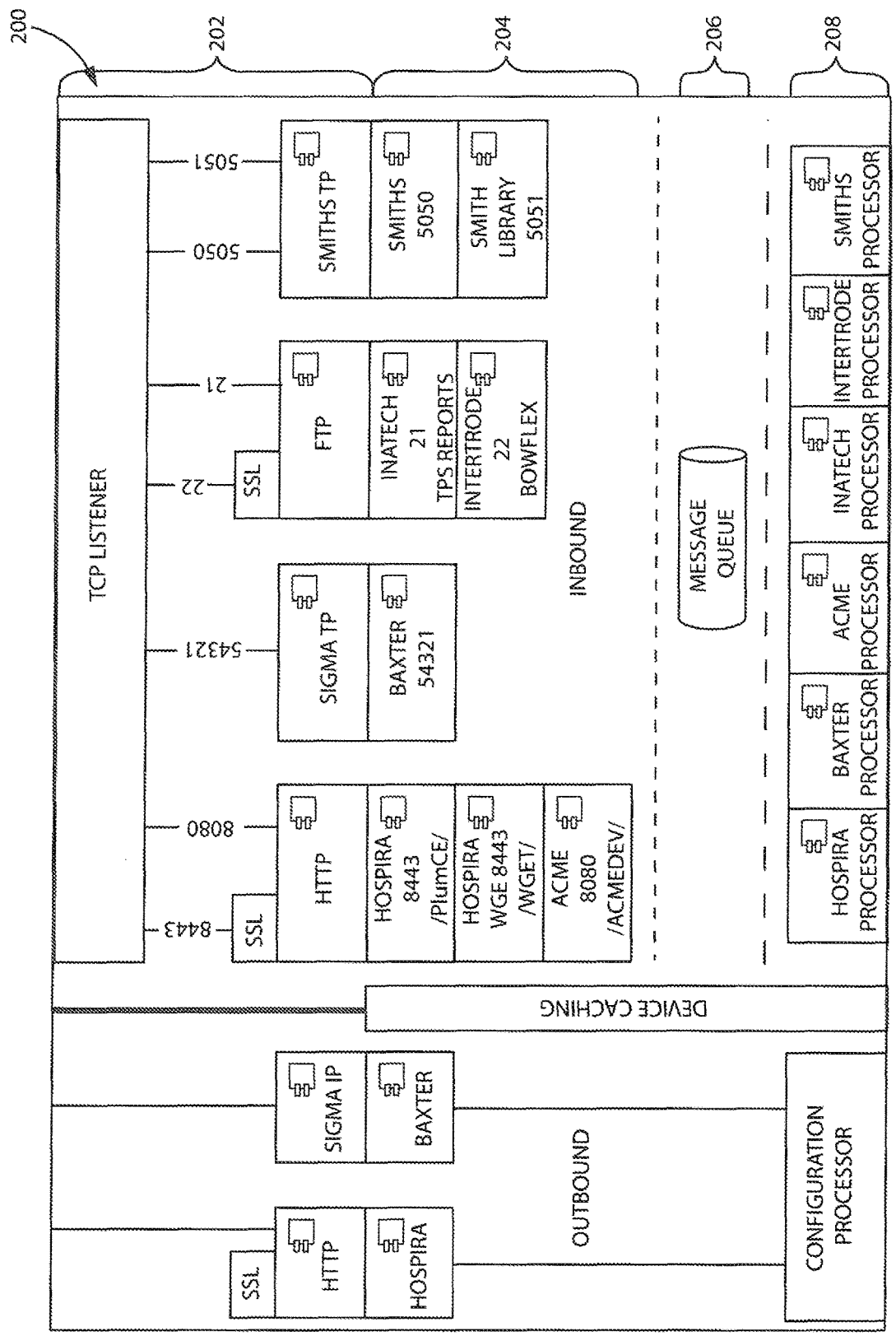
FIG. 2 is an illustration of a device communicator and processor of FIG. 1, configured to facilitate device communication with a large number of possible devices and communications engines, is shown according to an exemplary embodiment.

Referring now also to FIG. 2, device communicator and processor 200, configured to facilitate device communication with a large number of possible devices and communications engines, is shown according to an exemplary embodiment. For example, different devices from different manufacturers may all communicate on the same IP address and/or port. This is accomplished through custom device operating systems, firmware, operating libraries, etc. which can all be handled differently on different devices. Different devices may employ unique protocols and/or handshakes and therefore are all completely different.

It is the inventions objective to allow all these different devices including modular solution built around a common core engine. Device communicator and processor 200 may be implemented as a computer software application including instructions performed by the processor described above with reference to FIG. 1. Device communicator and processor 200 may be a single service that can be installed on several servers in a high availability, fault tolerant configuration. The core engine may be licensed as part of the standalone products or compile directly into a solution for a customer specific device.

The invention may include a native protocol that device manufacturers could adapt based on their type of device. Each module may include a reporting engine and an integration engine. The module may support multiple devices such as infusers, respirators, monitors, etc. as well as multiple transports. The device communicator and processor 200 includes a plug-in architecture for implementing transfer protocols 202, preprocessors 204, message queuing and durable storage 206, and device specific processing modules 208. These modules can be loaded at service start up and inserted/removed during runtime.

Preprocessors 204 will register with a transfer protocol 202 by sending it a port, using a secure socket layer (SSL) flag, using an option IP address, and providing a series of bytes that can be used as a signature to identify the message type. This data will be used by the transfer protocols 202 to route the message to the correct preprocessor 204. Transfer protocols 202 will listen for data on all the preprocessor registered ports and try to match the signature data that is registered for each individual port. Transfer protocol 202 will then send the data to the appropriate preprocessor 204. If only one preprocessor 204 registers for one port in the transfer protocol 202, no matching will occur and the data will be passed directly from the transfer protocol 202 to the preprocessor 204.

Preprocessors 204 are configured to read the message data to find a device identifier and compared to a list of known devices. The devices known to unauthorized, or if the device is unknown, it will reject the message and send an unauthorized device message through the system messaging to 112, shown above with reference to FIG. 1, so that another system can potentially use the messages. If the preprocessor 204 is not the owner of that device, preprocessor 204 is configured to query the state service 106 for the name of an alternative device communicator and processor 200 that is the owner of the device and notify that system to give up control. Preprocessor 204 will then signal the new device processor 200 to start processing for that device.

Preprocessors 204 are configured to store authorize message in the message queue for that device in the message queue durable storage 206. During message storage and formulation, preprocessors 204 will provide functions such as duplicate message detection.

Device processors 208 are configured to pull messages out of the messaging queues 206 and process the messages in order to translate them into a ViNES specific device, properties, action, metric, or alert object, further described below with reference to FIG. 3. Device processors 208 are further configured to store a processing state object to the state service 106 in case the processor system 200 fails and the processing needs to occur on another processor 200. Once a device processor 208 has enough information to translate messages to a ViNES object or property, it will save that ViNES object or property to the state service 106. The device processor 208 will be able to set "do not save state", "nonpersistent," and "non-transactional" flags on a message in order to bypass durable storage and guaranteed delivery processes. In the simplest configuration, a device processor 208 may be configured to send a device's raw messages as a RawMessage object.

Referring again to FIG. 1, state service 106 is a computer application configured to store and provide access to objects that are used by various services of the system 100. As processing of messages occurs, properties are saved to a central state service 106 such that, in the case of a DCP 200 failure, another DCP 200 can take over from where the last one left off. Accordingly, the state service 106 will transmit the state of a device and is objects in response to a query from any other service of the system 100. State service 106 will store processing state objects and ViNES objects for all device processors 208.

State service 106 is further configured to inject messages into the publish and subscribe service 104 based on a detected change to the ViNES object. Once a device processor 208 has determined that no more updates will occur to the top-level object, the device processor 208 will mark as complete, and the state service 106 will then send a final object complete message using publish and subscribe service 104 and delete that object. State service 106 will send a message to the publish and subscribe service 104 if the "non-transaction" flag is set in the ViNES object and will bypass the guaranteed message delivery process and make transmitting the data faster. Similarly, state service 106 will mark a message as nonpersistent if the "nonpersistent" flag is set. State service 106 will further transmit a message to the publish and subscribe system 104 constructing the system to not save the message to disk. Although this can lead to data loss if the system were to be stopped while message was only in temporary memory, this would make transmission of the data faster.

Publish and subscribe service 104 is a computer application configured to send out state change messages to interested systems. Publish and subscribe service 106 allows interested systems to subscribe to a set of object properties in order to receive data from objects that match those properties. The properties that can be subscribed include at least device ID object type, group ID, and transaction ID. System 100 will allow for different devices to store different data in a system 200 database (not shown). According to an exemplary embodiment, data is stored in historical data service 102 using key value pairs, and the definitions for this data are included in the plugins in processors 208. Each device may have a specific 'template' in the database. For instance, all infusion devices would have a standard template for the data. There can be a method or unique file format that allows for industry-standard data (such as standards being developed by IEEE) but system 200 may also allow for device or manufacturer specific data.

Accordingly, data from different devices is stored in the database in a common format, allowing systems to 'subscribe' to the data based off of a certain parameter—patient name, patient ID, room number, bed number, hospital floor, unit, specific hospital, etc. System 200 amalgamates data from a larger number of disparate types and manufacturers for devices into a meaningful report or analytic based off a common identifier.

For example, a caregiver may like to see the infusion, heart rate, temperature and oxygen saturation readings for a specific patient for the past 24 hours. Accordingly, the caregiver is able to subscribe to a set of linked datapoints that provide a replay of a patient's condition over long (+3 days) period of time without having to log into each unique system for the devices, find the data and then compile all of it manually. Today, the majority of this data is either lost or stored in disparate databases and systems, making it all but impossible to retrieve without significant effort in time and resources. System 200 is designed to simplify this process.

Publish and subscribe service 104 further allows a system to request the current state of all objects currently subscribed to that system even in advance of receiving state changes messages for those objects. A subscriber can further create a persistent message queue which would allow the accumulation of messages even if the system that is subscribing is off-line. A subscriber may further be able to re-create a ViNES object using the state change updates of that object supplied by the state service 106.

Binder service 109 is a computer application to provide binding between patients and medical devices and/or locations. Binder service 109 is configured to provide a data structure for mapping unique patient identifiers to unique medical device identifiers and/or location identifiers.

In operation, a medical system or devices, such as a patient monitor, may be preloaded with a medical device and/or location identifier. These monitors may be considered to be at fixed location with a unique device identifier. As a patient enters a bed location, the patient monitor may be manually loaded via a user interface, such as via a computer interface, tablet, laptop, smart phone, or other device, with a patient Medical Record Number ("MRN"), first name, last name and/or other identifying information. Device data can be received by the ViNES application 100, such as via an IIC (or I²C) Plug-In interface.

As messages arrive, they are analyzed for incoming patient binding information. A list of patients may be maintained, for example, in a local patient cache, such as in the IIC Plug-In interface. The MRN may be read from each incoming message, and if the MRN is not in the local cache, then the a query to a Binder API may be made. If the MRN is not in the Binder API, then the MRN, first name, last name and/or other identifying information may be added to Binder API and a local cache entry may be made in the Plug-In interface. If the MRN is in the Binder API, then only a local cache entry might be created in Plug-In interface.

Message may then be sent to the state service 106, where it can be published to various consumers. Historical data service 102 may consume a copy of the message. An Integration Output Queue may also consume a copy of the message.

ADT information, such as an "HL7 ADT" feed, may also be received, such as by periodically polling every 60 seconds a centralized database. This may be accomplished, for example, using a prepared application such as that provided by Mirth Corporation. If a new patient is detected, the prepared application may query the Binder API. If a patient exists, the patient may be updated if demographics are different. Patient demographics from an ADT feed may supersede patient monitor information. Location information from a patient monitor feed may supersede ADT information. If patient does not exist, it is created. If a patient update is detected, demographics may be updated in an existing record.

When a device message is sent out, it may be merged with patient information as maintained in the Binder service. Properly bound device/patient information may be sent for to an analytics module for determining analytic information about the patient based on the message, such as Etiometry in JavaScript Object Notation ("JSON") format via a web service post.

A notification system could also be provided to send notifications following certain events, such as not receiving an ADT feed, or not receiving expected information from an ADT feed. For example, device data could be received from an ADT feed without a corresponding patient identifier, which may indicate an incorrectly entered patient identifier or delayed ADT feed. Also, a mismatch between patient information provided by a medical device and patient information provided by an ADT feed may occur. A rule set may be implemented to address these possibilities, including requiring use of information provided by the ADT feed to be primary over information provided by the medical device. Additional messaging information could also be retained for conflict detection.

Configuration service 110 is a computer limited application configured to provide an asynchronous device update, such as updating a drug library stored on a device, as well as perform additional processing and tracking functions described below. Configuration service 110 is configured to receive configuration requests from other services of the system 100 and order to send data to a device. The configuration requests may include any type of configuration from "set screen color" to "upload firmware." Configuration 110 is configured to request and confirm successful updating configuration information by the device. Configuration service 110 is further configured to transmit queries to state service 106 to determine which DCP 200 is currently responsible for device and thereafter send that DCP 200, the configuration request. Thereafter, the DCP 200 and will respond the configuration service 110 with status information for the configuration request.

Binary service 108 is a computer implemented application configured to hold large binary objects that can be referenced within system messages, such as the aforementioned drug library file, firmware files, etc. Objects like an infuser drug library file will be loaded into the binary service 108. When a service needs access to this binary, for example during a drug library update, described above with reference to configuration service 110, the service was supply a binary 1D and received the binary object. Binary service 108 may further be utilized if a device sends large data such as images or sound files.

Historical data service 102 is a computer implement application configured to store historical data provided by the state service 106. Historical data service 102 can be configured to allow subscription to any combination of object properties and receive state updates from the publish and subscribe service 104. Thereafter, service 102 will then store the updates into a system database (not shown) such other services can access the historical object database.

Figure 3:
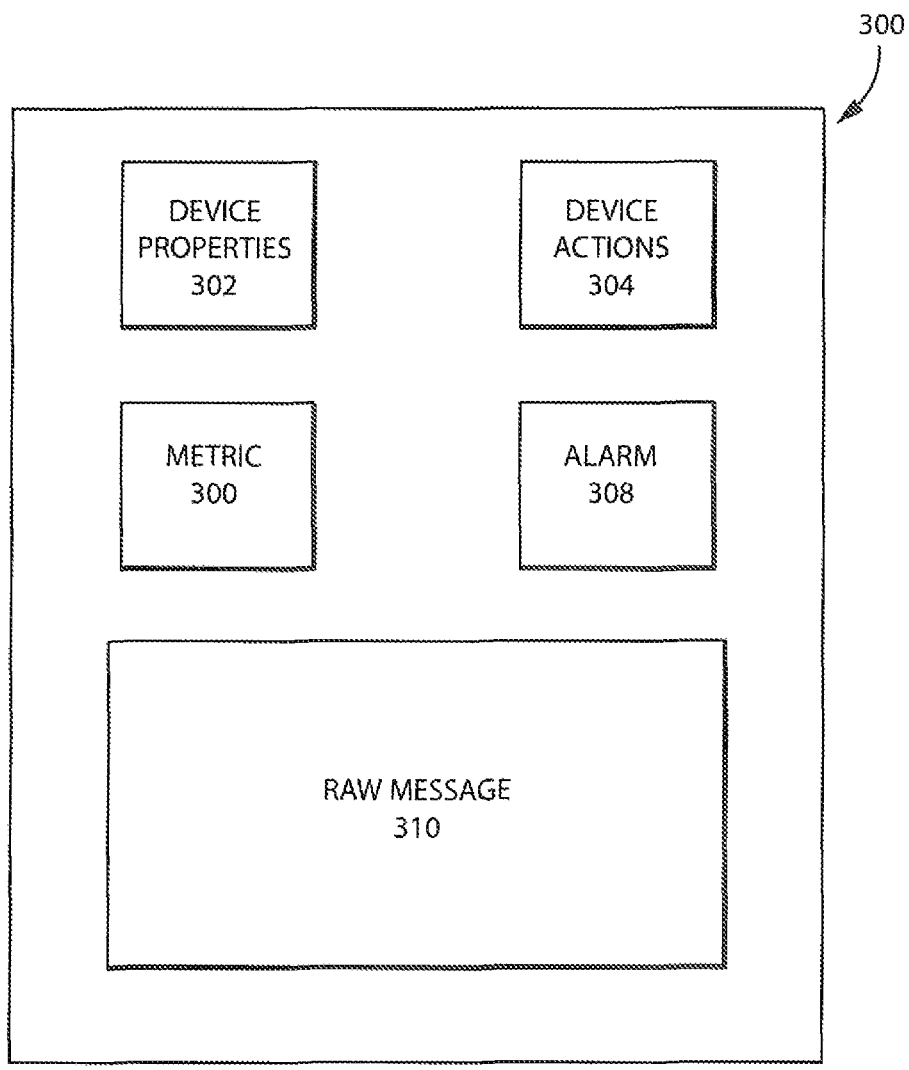
FIG. 3 is a depiction of an exemplary ViNES object, a computer implemented record stored in non-transitory memory of the system of FIG. 1, according to an exemplary embodiment.

Referring now to FIG. 3, an exemplary ViNES object 300, is a computer implemented record stored in non-transitory memory of the system 100, according to an exemplary embodiment. Object 300 is configured to include a device properties record 302, device actions record 304, a metric record 306, an alarm record 308, and a raw message 310 data field. Device properties record 302 is configured to hold the properties of device such as, but not limited to, IP address, serial number, etc. The device actions record 304 is configured to include a listing of objects that represent actions that may be taken by a device associated with records such as, but not limited to, infusion, ventilation, etc. Metric record 306 holds the property of a patient measurement. Alarm record 308 holds objects that represent alarms generated by a device. Raw message data field 310 is configured to include a raw message from a device.

Referring again to FIG. 1, the information that each module in DCP 200 outputs may be received by one or more of an integration engine, a reporting database, a custom dashboard, etc., the integration should support various protocols including IHE PCD01 for messages, IHE PCD02 for subscription, IHE PCD03 for auto programming features, IHE PCD09 for user definable alarms, the ability to connect to existing software such as Cerner and Epic, and support universal medical device communication standard. If no universal medical device communication standard exists, the invention may be used as a model for such a standard.

A website may allow users to login and access the stored information as well as manage the devices. There may be a single site at a hospital that could work for any device regardless of the particular brand or type of device. Reports may then be generated that each device that are accessible through the website.

The interface that allows users to use the invention may include a web based interface that is accessible through the Internet. The interface may also be able to accept branding or skins that allow certain manufacturers to add desired looks or visual appearances to the interface.

Security measures may also be employed to the interface such as internal forms based security and LDAP-based security. Full enterprise-wide organization, region, group, facility, users, and role architecture may also be employed in order to establish predetermined hierarchies for potential users. The interface may also allow for localization or internationalization allowing it to be used in any particular country or region. Interface may also be adaptable allowing for mobile phone or smart phone compatible display. Stored data may also be filtered so that the data that is displayed may be tailored to make more sense to the user. The interface may also include device configuration and auto configuration utilities that allow it to be set up and administer with minimal setup time and input from the user. The interface may also allow files to be distributed, also known as pushed, to the various devices which include operating system updates, firmware updates, drug library updates, configuration files, etc.

2. Detailed Description of Preferred Embodiments

The present invention and the various features and advantageous details thereof are explained more fully with reference to the non-limiting embodiments described in detail in the following description.

Figure 4:
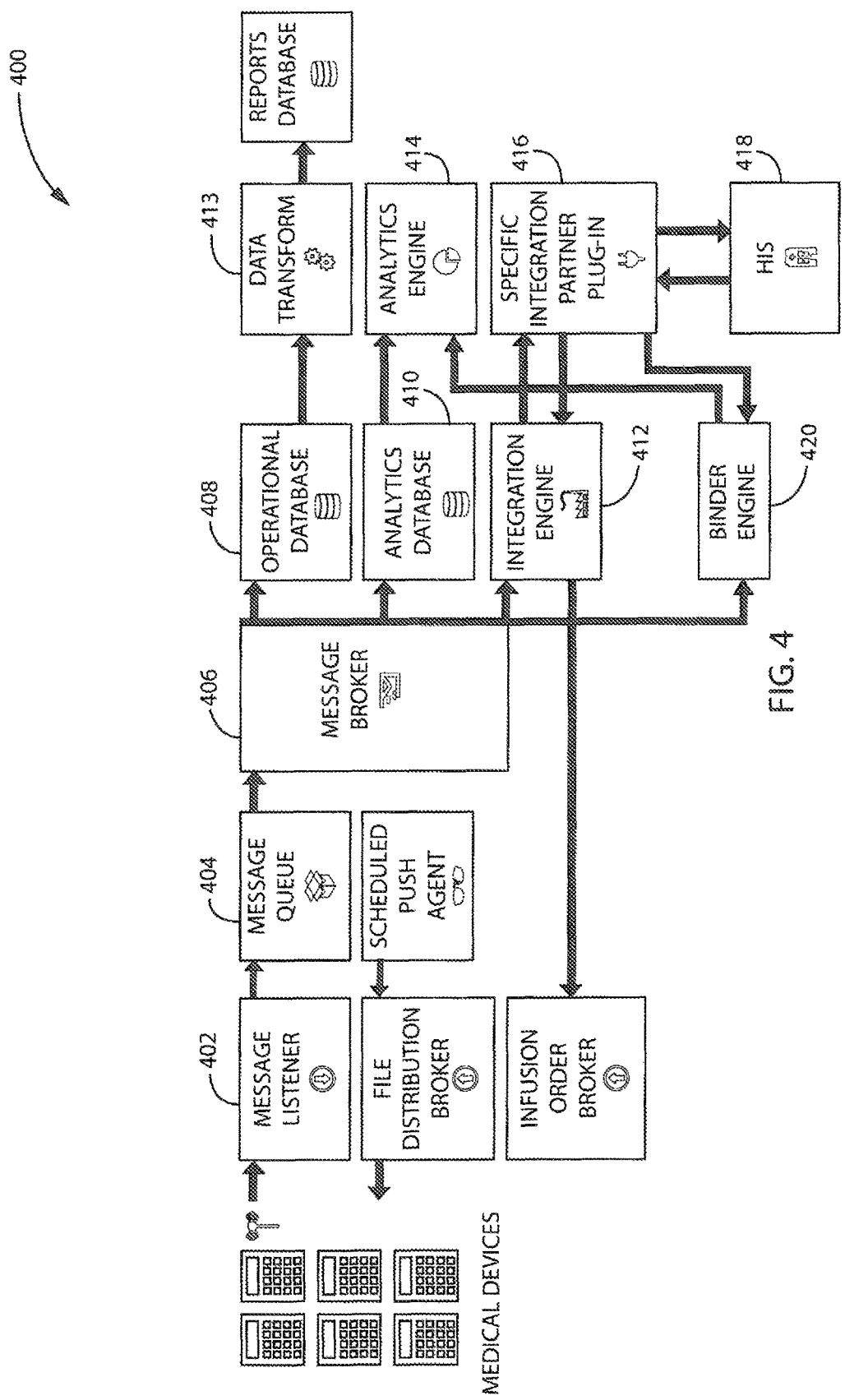
FIG. 4 is a flowchart illustrating how the system of FIG. 1 integrates with hospital infrastructure, according to an exemplary embodiment.

In accordance with the invention, FIG. 4 is a flowchart illustrating a computer implemented method for how medical devices wirelessly transmit information to a message listener. These methods may be implemented by one or more of the systems shown in FIG. 1 in combination with external devices and systems.

Referring first to FIG. 4, method 400 includes a message listener may include software loaded on a computer that is programmed to receive information in the form of a message regardless of the source in a step 402. A few examples of a medical device that may send a message to the message listener include, but are not limited to, an MRI machine, an x-ray machine, a medical liquid pump, and ultrasound machine, a heart rate monitor, a telephone, a fax machine or any other device that is used in the medical field.

After receiving a message the message listener may store the messages in the message queue in a step 404. A message broker may be programmed to distribute messages to multiple locations in a step 406. These multiple locations may include but are not limited to a operational system database 408, an analytics database 410, a binder engine 420, and integration engine 412. The main system database may perform ETL on the received messages in order to generate reports that are stored in a report database in a step 413. The analytics engine 414 may process and display real-time analytics from the data stored in the analytics database. The integration engine 416 may be coupled with a specific integration partner plug-in in order for the data to be accessible and used by the main hospital information system 418. The binder engine 420 may be coupled with one or more of the aforementioned modules, such as the message broker in step 406, the analytics engine 414, and the integration engine 416, to provide binding and/or unbinding services between patients and devices and/or locations. The main hospital information system may include but is not limited to Cerner, Epic, McKesson or other similar programs.

Figure 5:
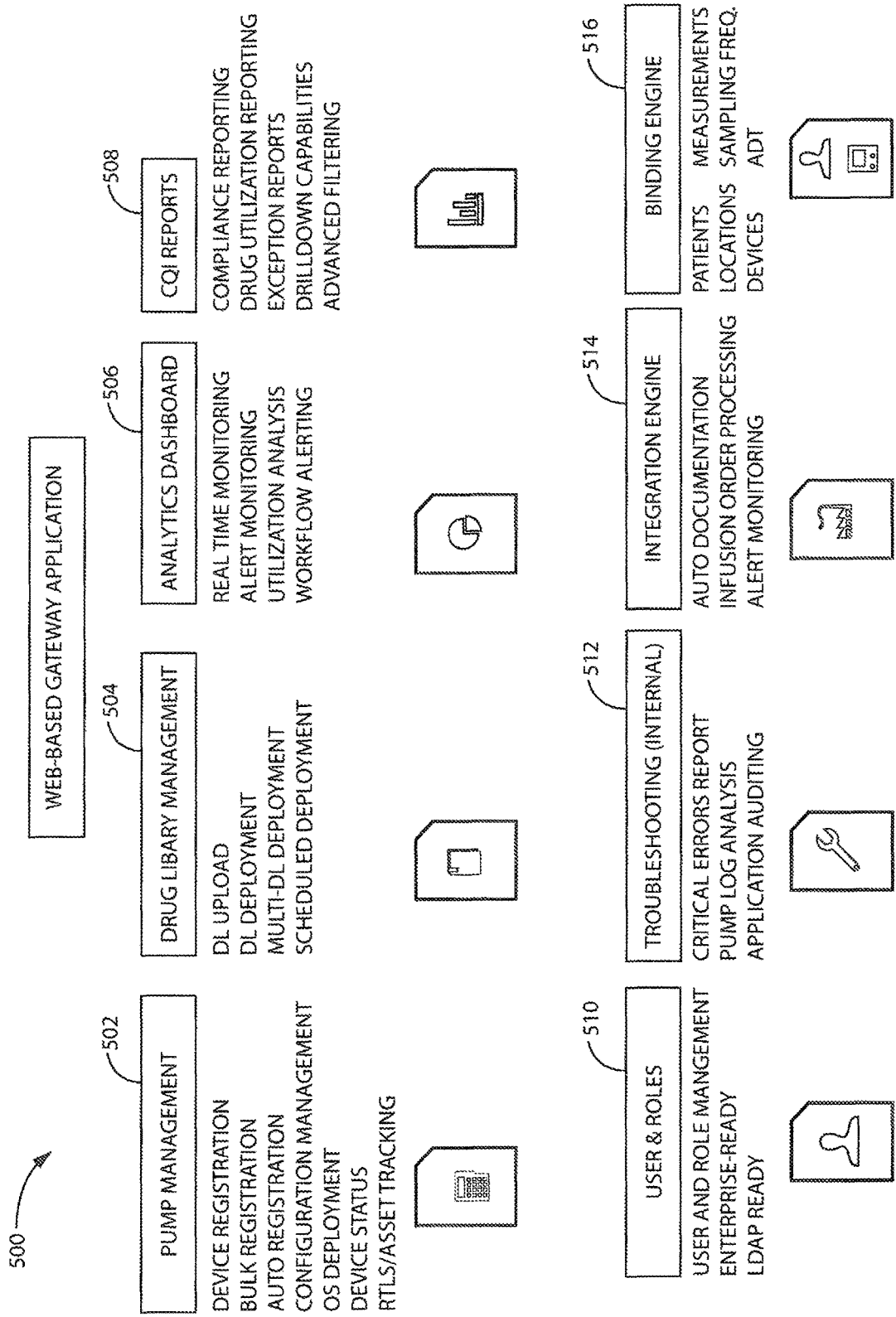
FIG. 5 illustrates an interface for interacting with and controlling the operation of the system of FIG. 1, according to an exemplary embodiment.

Referring now to FIG. 5, a block diagram is provided that describes a computer implemented gateway application 500 describing how the main hospital information system may then communicate with the specific partner plug in for generating orders for the medical devices. The integration engine passes these orders to an infusion broker, when an infusion pump is the device, and the push agent queues files to be distributed by the file distribution broker. For example, in one embodiment the medical device may include the medical liquid pumps for the administration of liquid drugs to patients. The system may be designed to integrate any manufacturer's brand of pump to ambulatory and hospital information systems. The system may be generic and allow connectivity to any manufacturer's pump.

Referring now to FIG. 5, a web based Gateway application 500 may be used so the system may manage all the medical systems or devices such as, for example, pumps in an organization including the pumps located in ambulances and hospital rooms. The following features may therefore be accessible at any time with internet access to the central database, or cloud.

Pump management 502 may be utilized to auto register, bulk register, keep track of the various pumps in the field including configuration management, operating system deployment, device status, and asset tracking. The web based Gateway application may also push operating system updates automatically and wirelessly to each pump. The message broker may be used to wirelessly push an infusion order to the pump notifying the medical personnel to administer a drug to a patient. The pushed messages may also include drug library management information that includes an entire library of drug information 504. The drug library may be periodically updated through scheduled deployments by the system and may be uploaded or downloaded to each device.

The system may also wirelessly monitor each pumps operation in the field to assist in the hospital in tracking the utilization of every pump in the field using CQI reports 508 as well as allow for real-time monitoring in the hospital by any authorized personnel identified by users & roles database display 510. The pumps may be further programmed to wirelessly transmit alerts to the system in order to notify qualified hospital personnel that an infusion order was properly carried out, was failed to be carried out, or that the patient's vitals reached a predetermined threshold. Workflow may also be monitored and alerted though an analytics dashboard application 506.

An added feature may include programming every pump in the field to calculate quality reports detailing the drug utilization, drilldown capabilities, advanced filtering, and compliance with any predetermined requirements, expectation reporting, or any other benchmark the hospital chooses to monitor.

This system may also wirelessly update each pump in the field to allow certain users access to operate the pump. Different users may be assigned different authorizations in database 510. The system may also be LDAP ready and enterprise ready allowing seamless integration with existing hospital IT infrastructure.

The system may be updated, repaired, or serviced wirelessly by an authorized party using troubleshooting interface 512. This allows for remote third-party troubleshooting and auditing should any problems arise in the field.

The integration engine 514 may also allow for auto documentation regarding order processing and alert monitoring.

The binding engine 516 may provide binding and/or unbinding services, including as described above with respect to FIGS. 1 and 4.

Figure 6:
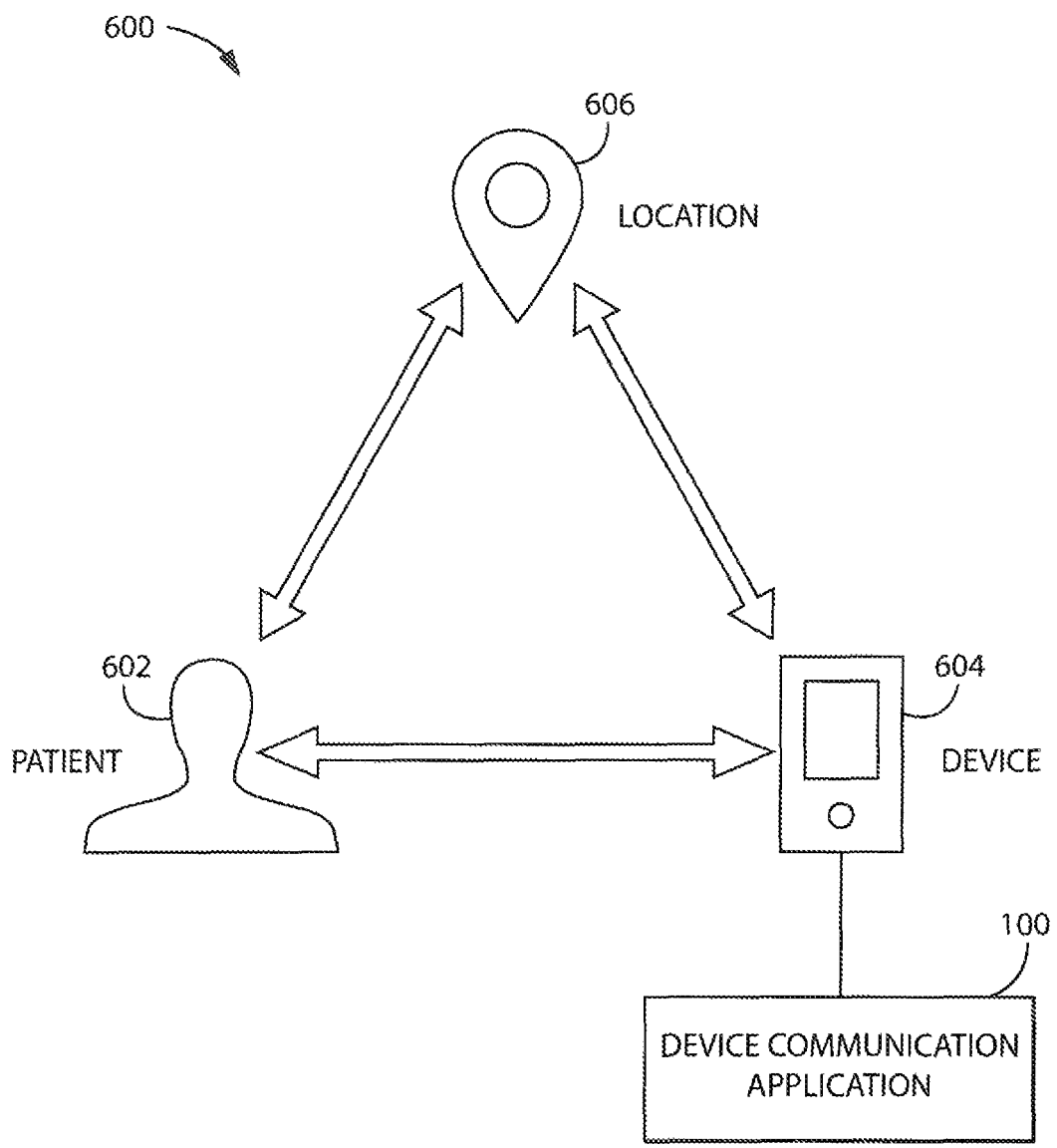
FIG. 6 is a depiction of binding according to an exemplary embodiment.

Referring now to FIG. 6, a depiction of binding 600 according to an exemplary embodiment is provided. A patient 602 may be identifiable by a unique patient identifier; a medical device 604 may be identifiable by a unique medical device identifier; and a location 606 may be identifiable by a unique location identifier. Accordingly, the patient 602 may be bound to the medical device 604 and/or the location 606, and the medical device 604 may be bound to the location 606. In addition, the patient 602 may be bound to additional medical devices at the same location 606 and/or other medical devices at other locations. The patient 602 may also be bound to all medical devices at the location 606 and/or all medical devices at another location. Binding effectively provides a data structure mapping, for example, patient identifiers to medical device identifiers and/or location identifiers.

In turn, messages from the medical device 604 may be sent to the ViNES application 100. In an embodiment, received electronic message from medical devices of different types may be linked together based on medical device identifiers of the received messages mapping to a common patient identifier in the data structure. The ViNES application 100, or module thereof, may store such messages, including patient measurement values contained therein, in a common storage element such as a database.

Figure 7:
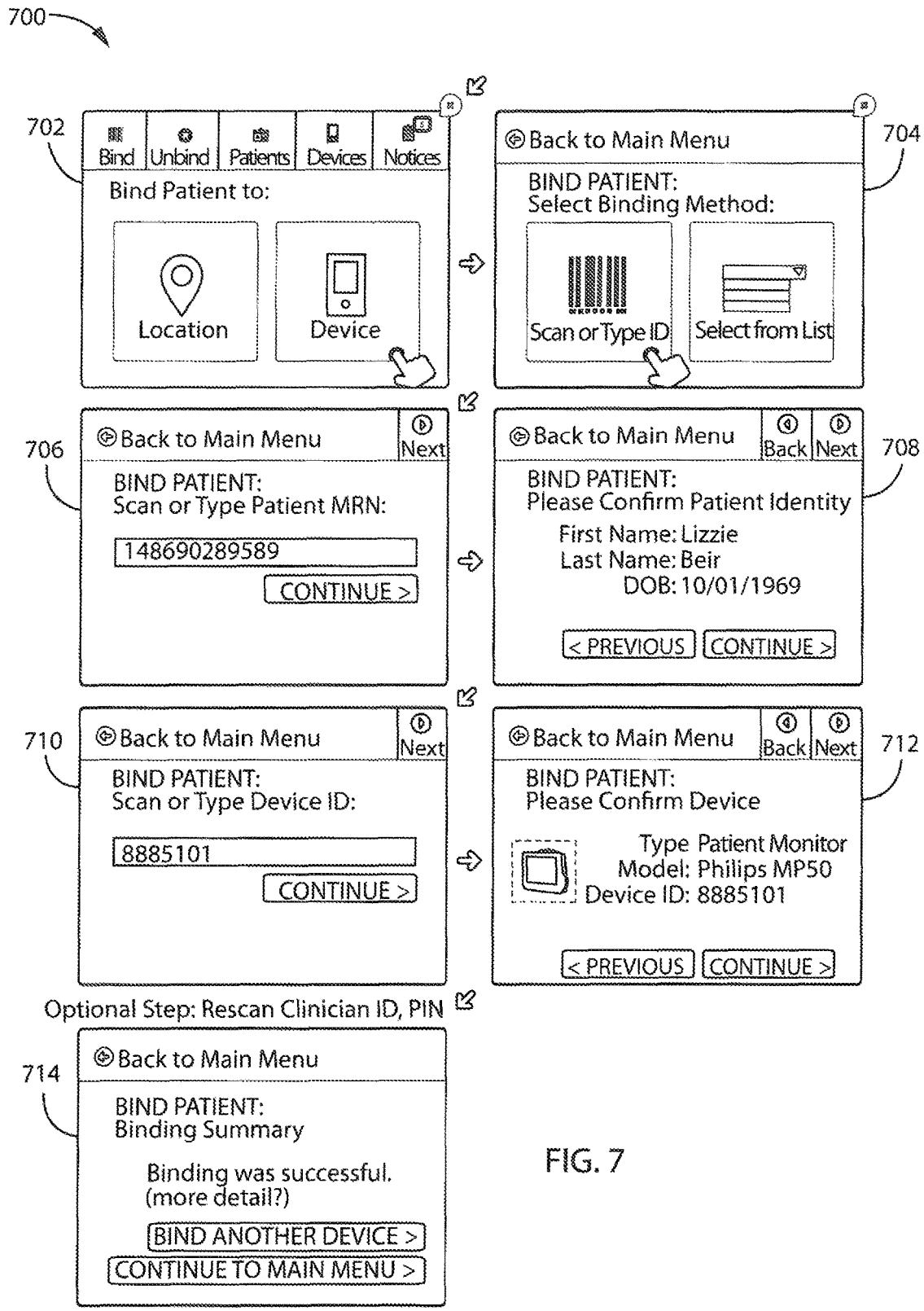
FIG. 7 is a flowchart illustrating an example of binding a patient to a location or a device according to an exemplary embodiment.

Referring now to FIG. 7, a flowchart illustrating an example of binding 700 a patient to a location or a device according to an exemplary embodiment is provided. In step 702, following secure login by a clinician via a user interface, the clinician may select to bind a patient to a location or device. A location may be selected, for example, to bind a patient to all devices at a location, whereas a device may be selected, for example, to bind a patient to a particular device at a given location. Upon selecting a device, for example, in step 704, a method for binding may be selected by choosing to scan (such as a barcode) or type a medical identifier for the device, or by selecting a device from list of previously entered devices. Next, in step 706, a patient identifier may be entered, such as by manually typing the patient's identifier or scanning the patient's identifier, and in step 708, the patient's identity may be confirmed. Next, in step 710, a device identifier may be entered, such as by manually typing the device's identifier or scanning the device's identifier, and in step 712, the medical device may be confirmed. Finally, in step 714, upon successfully binding the patient to the location or device, confirmation is provided.

Figure 8:
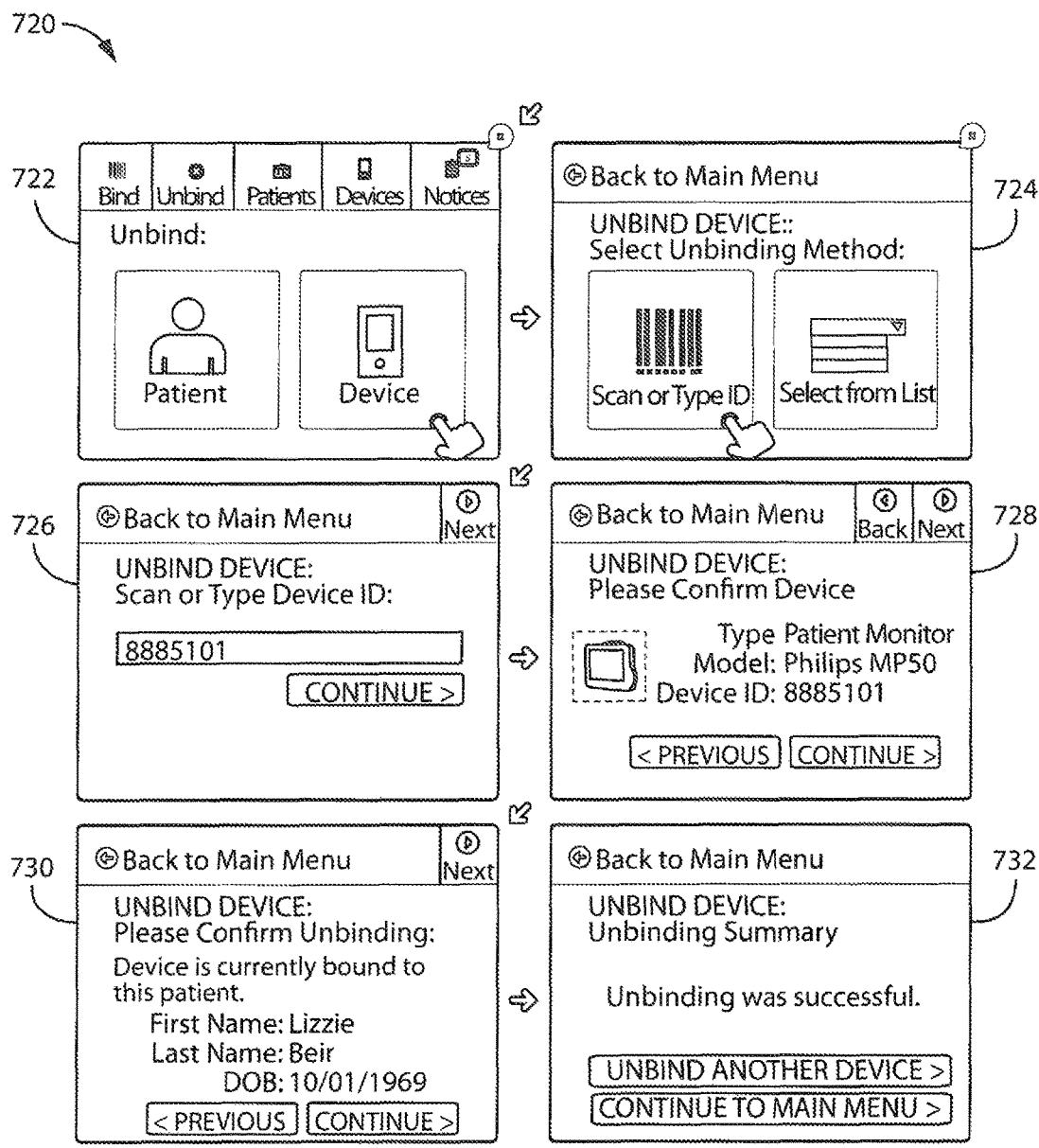
FIG. 8 is a flowchart illustrating an example of unbinding a patient from a location or a device according to an exemplary embodiment.

Referring now to FIG. 8, a flowchart illustrating an example of unbinding 720 a patient from a location or a device according to an exemplary embodiment is provided. In step 722, following secure login by a clinician via a user interface, the clinician may select to unbind a patient from a location or device. A location may be selected, for example, to unbind a patient from all devices at a location, whereas a device may be selected, for example, to unbind a patient from a particular device at a given location. Upon selecting a device, for example, in step 724, a method for unbinding may be selected by choosing to scan (such as a barcode) or type a medical identifier for the device, or by selecting a device from list of previously entered devices. Next, in step 726, a device identifier may be entered, such as by manually typing the device's identifier or scanning the device's identifier, and in step 728, the medical device may be confirmed. Next, in step 730, notification may be given that the selected device is currently bound to a particular patient, and a clinician may proceed to affirmatively unbind the device from the patient. Finally, in step 732, upon successfully unbinding the patient from the location or device, confirmation is provided.

Figure 9:
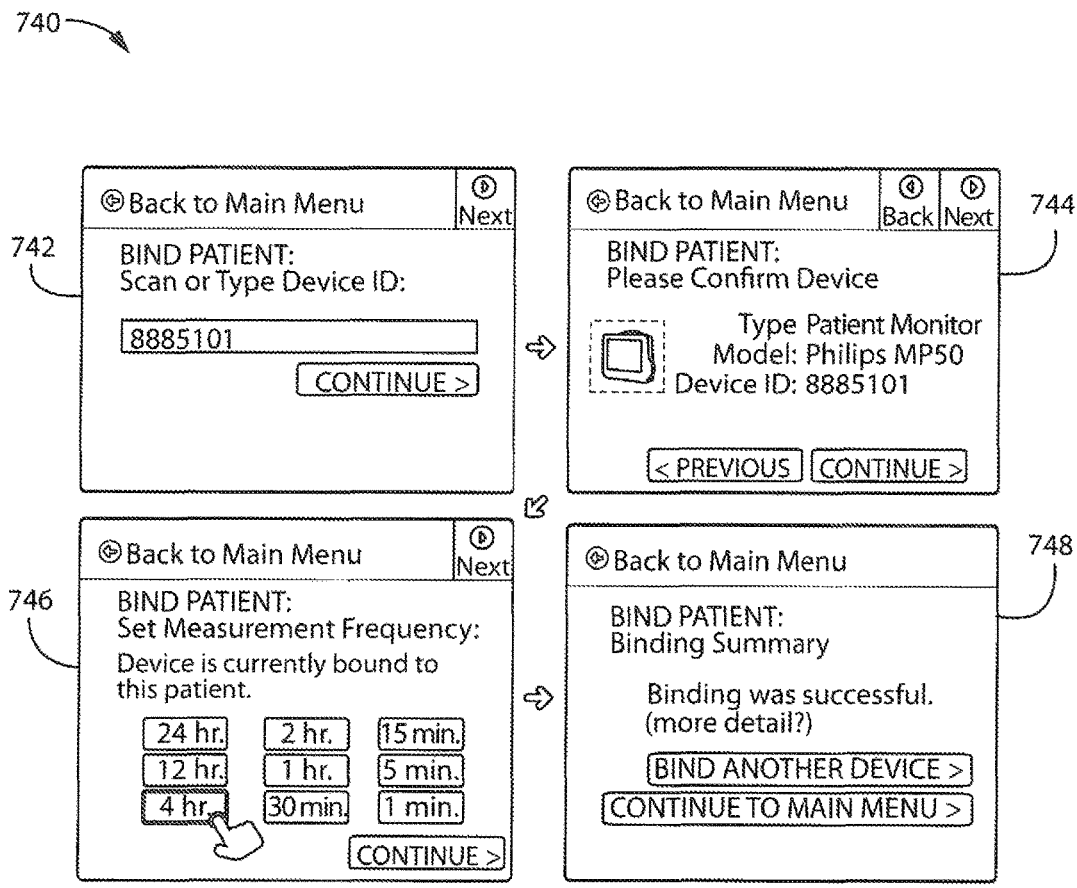
FIG. 9 is a flowchart illustrating an example of setting a measurement value sampling frequency according to an exemplary embodiment.

Referring now to FIG. 9, a flowchart illustrating an example of setting 740 a measurement value sampling frequency according to an exemplary embodiment is provided. During the initial binding process, or at a later time following a successful binding, a step 746 may be provided in which a selection is made for setting a measurement sampling frequency for a selected (bound) device. Measurements may be sent at specific intervals, such as every hour, or at specific times of the day, such as each-hour-on-the-hour. For example, a clinician may select to periodically receive messages including measurement values providing sampling data every 24 hours, every 12 hours, every 4 hours, and so forth. Such measurement values may provide recurring data such as, for example, a heartbeat measurement, a blood pressure measurement or a drug delivery measurement. A defined set of messages that contain a "measurement set" may be sent. Periodic settings could be applicable to either device group and/or an individual device by identifier.

Figure 10:
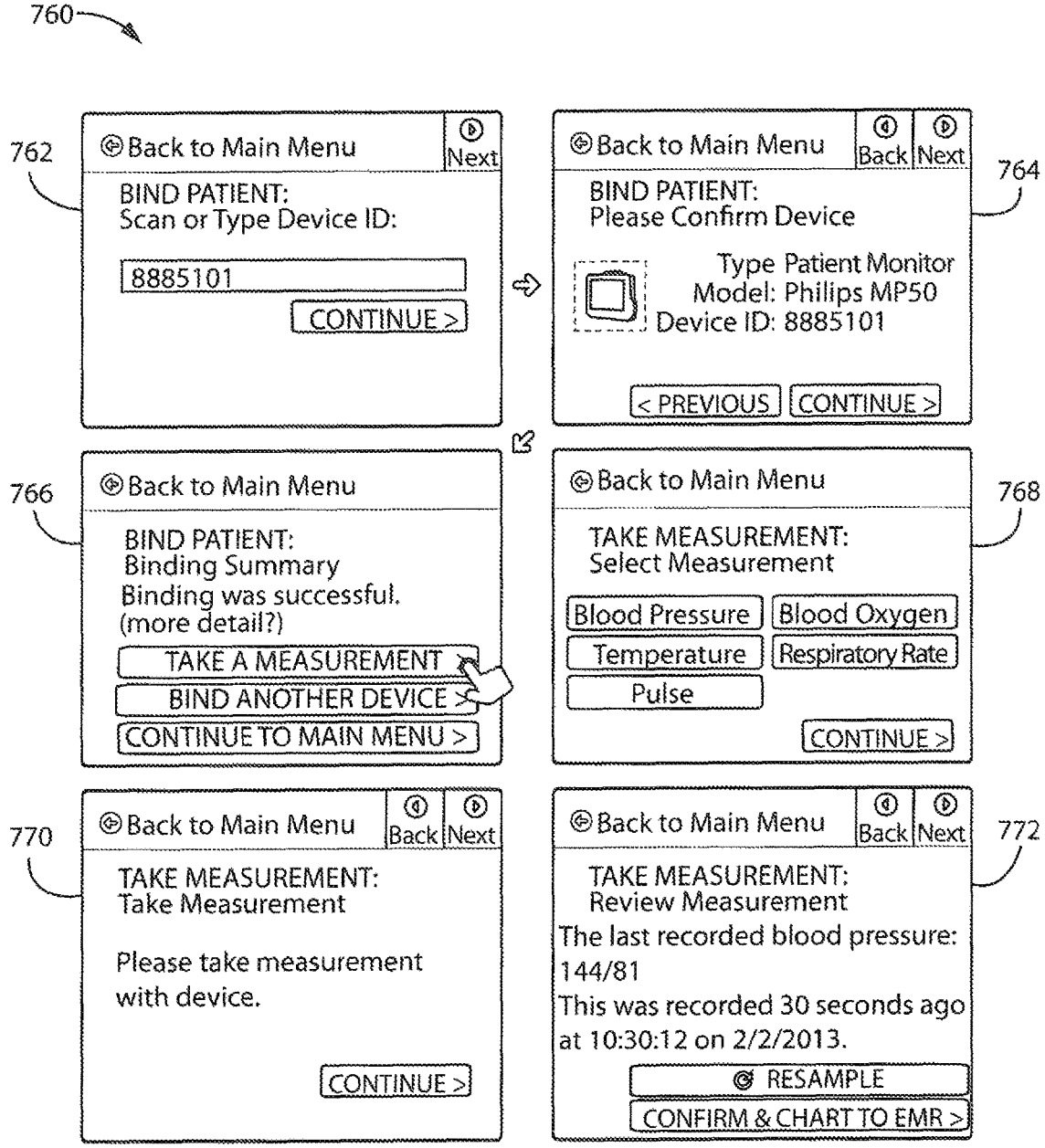
FIG. 10 is a flowchart illustrating sending a measurement value according to an exemplary embodiment.

Referring now to FIG. 10, a flowchart illustrating sending 760 a measurement value according to an exemplary embodiment is provided. During the initial binding process, or at a later time following a successful binding, a step 768 may be provided in which a selection a selection may be made for sending a measurement value from a selected (bound) device. For example, if a blood pressure monitor, a temperature sensor, a heartbeat monitor, a blood oxygen sensor and respirator are bound to a patient, the clinician may select to receive a measurement value corresponding to a blood pressure, a temperature, a heartbeat, a blood oxygen level and/or a respiratory rate for the patient, respectively. Next, in step 770, confirmation to take the particular measurement could optionally be requested before the measurement is sent, such as for a confirmed episodic integration versus an unconfirmed episodic integration. Finally, in step 772, the measurement value may be provided via the electronic message from the medical device.

Figure 11A:
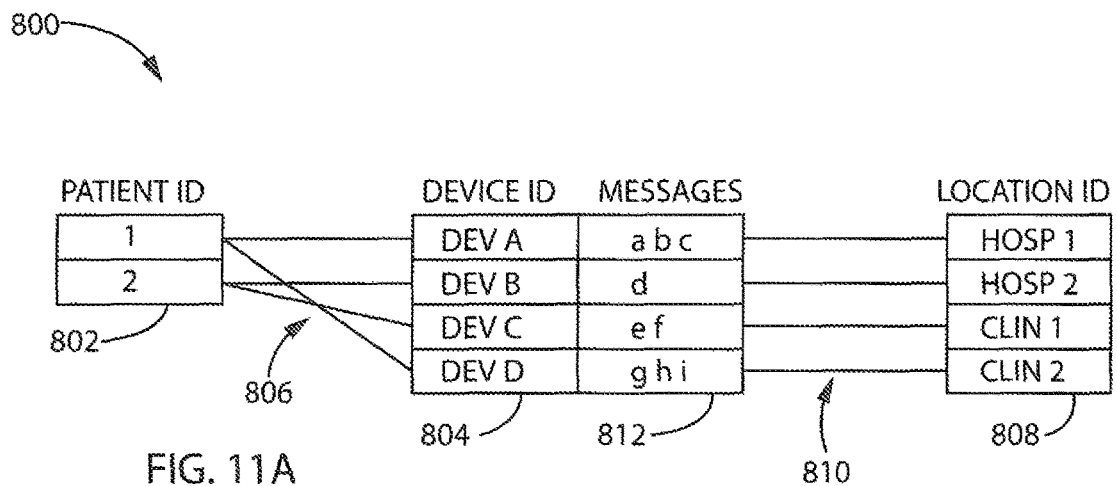
FIG. 11A is a block diagram illustrating binding based on device identifiers.

Retelling now to FIG. 11A, a block diagram illustrating binding 800 based on device identifiers is provided. A set of unique patient identifiers 802 corresponding to different patients may be mapped to a set of unique medical device identifiers 804 corresponding to different medical devices, some of which being of different types. The mapping 806 between the patient identifiers 802 and the medical device identifiers 804, which may be held in a data structure, may be simplistic or complex. For example, in a simple case as shown, "Patient 1" may be mapped to "Device A" and "Device D," and "Patient 2" may be mapped to "Device B" and "Device C." In a more complex case, many more patients may be provided, and/or each patient may be mapped to many more medical devices.

In addition, the medical device identifiers 804 may also be mapped to a set of location identifiers 808 corresponding to different physical locations for the medical devices. The mapping 810 between the medical device identifiers 804 and the location identifiers 808, which may be held in a data structure, may also be simplistic or complex. For example, in a simple ease, "Device A" may be mapped to "Hospital Room 1," "Device B" may be mapped to "Hospital Room 2," and so forth. In a more complex case, multiple devices may be provided at a single location, and/or a single device may be transportable between multiple locations.

Each medical device may electronic messages 812, which messages may include patient measurement values. For Example, "Device A" may send messages "a," "b" and "c," "Device B may send message "d," and so forth.

Figure 11B:
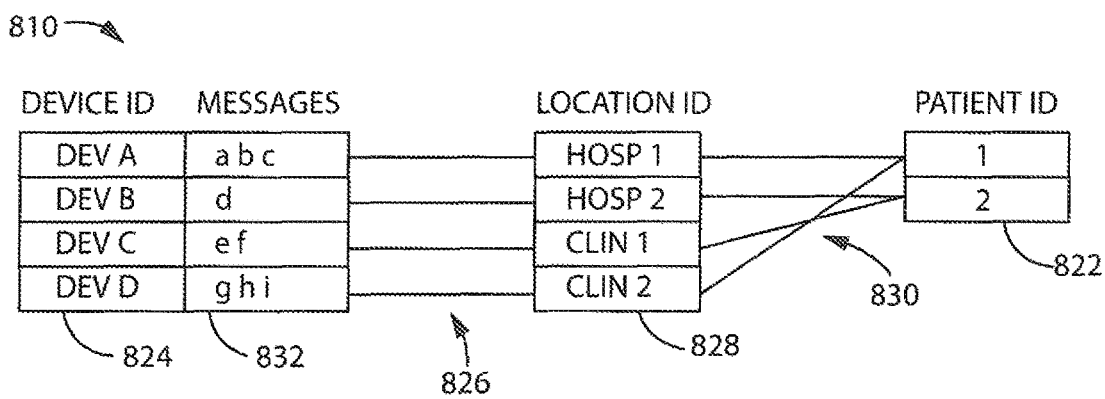
FIG. 11B is a block diagram illustrating binding based on location identifiers.

Alternatively, or in addition, referring to FIG. 11B, a block diagram illustrating binding 820 based on location identifiers is provided. In this case, a set of unique patient identifiers 822 corresponding to different patients may be mapped to a set of location identifiers 828 corresponding to different physical locations for the medical devices. The mapping 830 between the medical device identifiers 804 and the location identifiers 808, which may be held in a data structure, may also be simplistic or complex. For example, in a simple case as shown, "Patient 1" may be mapped to "Hospital Room 1" and "Clinic Room 2," and "Patient 2" may be mapped to "Hospital Room 2" and "Clinic Room 2." In a more complex case, many more patients may be provided, and/or each patient may be mapped to many more locations.

In addition, the location identifiers 828 may also be mapped to medical device identifiers 824 corresponding to different medical devices, some of which being of different types. The mapping 826 between the medical device identifiers 824 and the location identifiers 828 may also be held in a data structure, and the each medical device may communicate electronic messages 832 which may include patient measurement values.

Figure 11C:
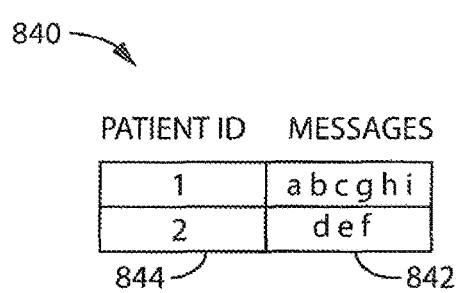
FIG. 11C is a block diagram illustrating linking messages to patient identifiers, each according to an exemplary embodiment.

Referring now to FIG. 11C, a block diagram 840 illustrating linking messages to patient identifiers, each according to an exemplary embodiment is provided. A binder service may operate to receive electronic messages 842 from the medical devices and link received messages from the medical devices based on the medical device identifiers of the received messages mapping to common patient identifiers 844 in the data structure. Alternatively, or in addition, the binder service may operate to receive electronic messages 842 from the medical devices and link received messages from the medical devices based on the medical device identifiers of the received messages mapping to a location identifier 828 corresponding to a common patient identifier 844. Accordingly, such linked messages, including the patient measurement values, may be stored in a common storage element, retrieved together based on providing the common patient identifier 844, and/or sent to an analytics module for determining analytic information about a patient based on the patient measurement values. In addition, update information with respect to patient identifiers, medical device identifiers and location identifiers may be received, which may affect, for example, binding and/or unbinding.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. Furthermore, all the disclosed features of each disclosed embodiment can be combined with, or substituted for, the disclosed features of every other disclosed embodiment except where such features are mutually exclusive. It is intended that the appended claims cover all such additions, modifications and rearrangements. Expedient embodiments of the present invention are differentiated by the appended claims.

What is claimed is:
1. A system for binding medical devices to patients, the system comprising:
a plurality of medical devices configured to implement differing communication protocols with respect to one another for communicating device specific messages, wherein each medical device includes a unique medical device identifier, and wherein each medical device is further configured to communicate a patient measurement value or a drug delivery measurement value; and
a computer in communication with the plurality of medical devices and a user interface, the computer executing a program stored in a non-transient medium to:
provide a selection to the user interface to bind a unique patient identifier corresponding to a patient to an infusion pump medical device of the plurality of medical devices or to a location corresponding to the infusion pump medical device of the plurality of medical devices;
upon receiving a response to the selection, map the unique patient identifier to a unique medical device identifier of the infusion pump medical device in a data structure, wherein the data structure further maps the patient identifier to a unique medical device identifier of a second medical device of the plurality of medical devices;
receive first and second device specific messages from the infusion pump and the second medical device, respectively, wherein each medical device provides a medical device identifier, and wherein the second device specific message includes a patient measurement value and the first device specific message includes a drug delivery measurement value;
translate the first and second device specific messages into first and second message objects, respectively, wherein the first and second message objects are provided in a common protocol with respect to one another;
link the first and second message objects originating from the infusion pump medical device and the second medical device, respectively, based on the medical device identifiers of the messages mapping to the patient identifier in the data structure;
compare the patient measurement value of the second message object to a patient measurement value of a second previous message object that is associated with the patient identifier and the drug delivery measurement value of the first message object to a drug delivery measurement value of a first previous message object that is associated with the patient identifier;

provide the first message object to a publish service if there is a change between the drug delivery measurement value of the first message object and the drug delivery measurement value of the first previous message object;

provide the second message object to the publish service if there is a change between the patient measurement value of the second message object and the patient measurement value of the second previous message object; and store the patient measurement value and the drug delivery measurement value of the linked message objects in a common storage element.

2. The system of claim 1, further comprising retrieving the patient measurement value and the drug delivery measurement value of the linked messages according to the patient identifier.

3. The system of claim 1, further comprising sending the patient measurement value and the drug delivery measurement value of the linked message objects to an analytics module for determining analytic information about the patient based on the patient measurement value and the drug delivery measurement value.

4. The system of claim 1, further comprising periodically receiving messages from at least one of the medical devices.

5. The system of claim 4, wherein the patient measurement values of the periodically received messages provide at least one of a heartbeat measurement, a blood pressure measurement and a drug delivery measurement.

6. The system of claim 4, wherein the periodically received messages are received every 24 hours or less.

7. The system of claim 1, further comprising receiving update information with respect to the patient identifier and to update the data structure accordingly.

8. The system of claim 7, wherein the update information is provided via an HL7 ADT (Admit Discharge Transfer) feed.

9. The system of claim 7, wherein the data structure is updated by removing a mapping between the patient identifier and the medical device identifier.

10. The system of claim 1, wherein each medical device also provides a location identifier and the data structure includes mapping patient identifiers to location identifiers.

11. A system for binding medical devices to patients, the system comprising:

a plurality of medical devices configured to implement differing communication protocols with respect to one another for communicating device specific messages, wherein each medical device includes a unique medical device identifier, and wherein each medical device is further configured to communicate a patient measurement value or a drug delivery measurement value; and a computer in communication with the plurality of medical devices and a user interface, the computer executing a program stored in a non-transient medium to:

provide a selection to the user interface to bind a unique patient identifier corresponding to a patient to a first medical device of the plurality of medical devices or to a location corresponding to a first medical device of the plurality of medical devices;

upon receiving a response to the selection, map the unique patient identifier to a unique location identifier of the first medical device in a data structure, wherein the data structure further maps the patient identifier to a unique location identifier of a second medical device of the plurality of medical devices;

update the data structure mapping to correspond unique patient identifiers to the location identifiers;

receive first and second device specific messages from the first and second medical devices, respectively, wherein each medical device provides a medical device identifier, and wherein the second device specific message includes a patient measurement value and the first device specific message includes a drug delivery measurement value;

translate the first and second device specific messages into first and second message objects, respectively, wherein the first and second message objects are provided in a common protocol with respect to one another;

link the first and second message objects originating from the first and second medical devices, respectively, based on the medical device identifiers of the messages mapping to the patient identifier in the data structure;

compare the patient measurement value of the second message object to a patient measurement value of a second previous message object that is associated with the patient identifier and the drug delivery measurement value of the first message object to a drug delivery measurement value of a first previous message object that is associated with the patient identifier;

provide the first message object to a publish service if there is a change between the drug delivery measurement value of the first message object and the drug delivery measurement value of the first previous message object;

provide the second message object to the publish service if there is a change between the patient measurement value of the second message object and the patient measurement value of and the second previous message object; and store the patient measurement value and the drug delivery measurement value of the linked message objects in a common storage element.

12. The system of claim 11, further comprising sending the patient measurement value and the drug delivery measurement value of the linked message objects to an analytics module for determining analytic information about the patient based on the patient measurement value and the drug delivery measurement value.

13. The system of claim 11, further comprising receiving update information with respect to the patient identifier and to update the data structure accordingly.

14. The system of claim 13, wherein the data structure is updated by removing a mapping between the patient identifier and the medical device identifier.

15. The system of claim 11, wherein each medical device also provides a location identifier and the data structure includes mapping patient identifiers to location identifiers.

16. A medical device communication system for binding medical devices to patients, the system comprising:

a plurality of medical devices configured to implement differing communication protocols with respect to one another for communicating device specific messages, wherein each medical device includes a unique medical device identifier, and wherein each medical device is further configured to communicate a patient measurement value or a drug delivery measurement value; and a computer in communication with the plurality of medical devices, the computer providing:
a user interface;
a data structure for mapping unique patient identifiers to unique medical device identifiers;
a communications port for receiving electronic messages from the plurality of medical devices;
a binding engine for linking received messages from the medical devices based on the medical device identifiers of the received messages being mapped to a patient identifier in the data structure; and
a storage element for storing patient measurement values and the drug delivery measurement value of the linked messages in a common location,
wherein the computer executes a program stored in a non-transient medium to:
provide a selection to the user interface to bind a unique patient identifier corresponding to a patient to a first medical device of the plurality of medical devices or to a location corresponding to a first medical device of the plurality of medical devices;
upon receiving a response to the selection, map the unique patient identifier to a unique medical device identifier of the first medical device in the data structure, wherein the data structure further maps the patient identifier to a unique medical device identifier of a second medical device of the plurality of medical devices;
receive first and second device specific messages from the first and second medical devices, respectively, through the communications port, wherein each medical device provides a medical device identifier, and wherein the second device specific message includes a patient measurement value and the first device specific message includes a drug delivery measurement value;
translate the first and second device specific messages into first and second message objects, respectively, wherein the first and second message objects are provided in a common protocol with respect to one another;
execute the binding engine to link the first and second message objects originating from the first and second medical devices, respectively, based on the medical device identifiers of the messages mapping to the patient identifier in the data structure;
compare the patient measurement value of the second message object to a patient measurement value of a second previous message object that is associated with the patient identifier and the drug delivery measurement value of the first message object to a drug delivery measurement value of a first previous message object that is associated with the patient identifier;
provide the first message object to a publish service if there is a change between the drug delivery measurement value of the first message object and the drug delivery measurement value of the first previous message object;
provide the second message object to the publish service if there is a change between the patient measurement value of the second message object and the patient measurement value of the second previous message object; and
store the patient measurement value and the drug delivery measurement value of the linked message objects in a common storage element.

17. The medical device communication system of claim 16, further comprising an analytics engine for receiving the patient measurement value and the drug delivery measurement value of the linked message objects to determine analytic information about the patient based on the patient measurement value and the drug delivery measurement value.

18. The medical device communication system of claim 16, further comprising inputting patient identifiers and medical device identifiers through the user interface for mapping.

19. The medical device communication system of claim 16, wherein the user interface is provided via a tablet computer.

20. The medical device communication system of claim 16, wherein each medical device also provides location identifier and the data structure includes mapping patient identifiers to location identifiers.

* * * * *